(12) United States Patent
Park

(10) Patent No.: US 8,467,864 B2
(45) Date of Patent: *Jun. 18, 2013

(54) SYSTEMS AND METHODS FOR USE BY AN IMPLANTABLE MEDICAL DEVICE FOR DETECTING AND DISCRIMINATING STROKE AND CARDIAC ISCHEMIA USING ELECTROCARDIAC SIGNALS AND HEMODYNAMIC PARAMETERS

(75) Inventor: Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 599 days.

This patent is subject to a terminal disclaimer.

(21) Appl. No.: 12/722,206

(22) Filed: Mar. 11, 2010

(65) Prior Publication Data

US 2011/0224555 A1    Sep. 15, 2011

(51) Int. Cl.
*A61B 5/0402* (2006.01)

(52) U.S. Cl.
USPC .......................................................... 600/513

(58) Field of Classification Search
USPC .................................................. 600/517, 526
See application file for complete search history.

(56) References Cited

U.S. PATENT DOCUMENTS

| | | | |
|---|---|---|---|
| 4,485,813 A | 12/1984 | Anderson et al. |
| 4,535,774 A | 8/1985 | Olson |
| 4,719,921 A | 1/1988 | Chirife |
| 4,733,667 A | 3/1988 | Olive et al. |
| 4,759,366 A | 7/1988 | Callaghan |
| 4,884,576 A | 12/1989 | Alt |
| 5,040,533 A | 8/1991 | Fearnot |
| 5,328,460 A | 7/1994 | Lord et al. |
| 5,800,467 A | 9/1998 | Park et al. |
| 6,044,299 A | 3/2000 | Nilsson |
| 6,050,952 A | 4/2000 | Hakki et al. |
| 6,208,900 B1 | 3/2001 | Ecker et al. |
| 6,468,263 B1 | 10/2002 | Fischell et al. |
| 6,788,970 B1 | 9/2004 | Park et al. |
| 6,937,896 B1 | 8/2005 | Kroll |
| 6,961,615 B2 | 11/2005 | Kroll et al. |

(Continued)

FOREIGN PATENT DOCUMENTS

EP    2215965 A1    8/2010

OTHER PUBLICATIONS

Khechinashvili, George et al., "Electrographic Changes in Patients with Acute Stroke: A Systematic Review," Cerebrovascular Diseases. 2002;14:67-76.

(Continued)

*Primary Examiner* — Carl H Layno
*Assistant Examiner* — Luther Behringer

(57) ABSTRACT

Techniques are provided for detecting and distinguishing stroke and cardiac ischemia within a patient using an implantable medical device. In one example, a preliminary indication of stroke is detected by a pacemaker or similar implantable device based on an analysis of features of an intracardiac electrogram (IEGM) sensed by the device. Exemplary IEGM features indicative of possible stroke include the onset of prominent U-waves, the onset of notched T-waves, and changes in ST segment duration or QT duration. Upon detection of a possible stroke, the device then detects one or more hemodynamic parameters that are typically affected by cardiac ischemia. Such hemodynamic parameters can include, e.g., cardiac contractility or stroke volume. The device then distinguishes stroke and cardiac ischemia from one another based on whether any changes detected in the hemodynamic parameters are consistent with cardiac ischemia. Implantable systems that exploit subcutaneous electrocardiograms (ECGs) rather than IEGMs are also described.

13 Claims, 8 Drawing Sheets

U.S. PATENT DOCUMENTS

| | | | |
|---|---|---|---|
| 7,099,718 | B1 | 8/2006 | Thacker et al. |
| 7,139,609 | B1 | 11/2006 | Min et al. |
| 7,235,530 | B2 | 6/2007 | Blair et al. |
| 7,297,114 | B2 | 11/2007 | Gill et al. |
| 7,502,644 | B2 | 3/2009 | Gill et al. |
| 7,524,287 | B2 | 4/2009 | Bharmi |
| 8,241,221 | B2 * | 8/2012 | Park .............................. 600/483 |
| 2006/0100530 | A1 | 5/2006 | Kliot et al. |
| 2007/0032736 | A1 | 2/2007 | Finnigan et al. |
| 2007/0276270 | A1 | 11/2007 | Tran |
| 2010/0198082 | A1 * | 8/2010 | Park .............................. 600/483 |

OTHER PUBLICATIONS

Yildiz, Ali et al, "ST-T changes in patients with acute ischemic stroke," Int J Cardiol. Apr. 17, 2009;133(3):397; author reply 398.

EP Search Report—EP Appl. No. 11154809.5.

NonFinal Office Action, mailed Apr. 4, 2011—Related U.S. Appl. No. 12/366,526.

Afsar, Nazire MD et al., "Acute Stroke Increases QT Dispersion in Patients Without Known Cardiac Diseases," Arch Neurol. 2003;60:346-350.

Bozluolcay, M. et al., Electrocardiographic findings and prognosis in ischemic stroke, Neurology India. 2003;51(4):500-502.

Carrera, E. MD et al., "Continuous assessment of electrical epileptic activity in acute stroke," Neurology. 2006;67:99-104.

Christensen, Hanne et al., "Abnormalities on ECTG and telemetry predict stroke outcome at 3 months," Journal of Neurological Sciences. 2005;234(1):99-103.

Dash, Monali et al., "ECG Changes in Pediatric Patients with Severe Head Injury," Journal of Neurosurgical Anethesiology. 2003;15(3):270-273.

Finnigan, Simon P. et al., "Quantitative ECG indices of sub-acute ischemic stroke correlate with clinical outcomes," Clinical Neurophysiology. 2007;118:2525-2532.

Finnigan, Simon P. et al., "Correlation of Quantitative ECG in Acute Ischemic Stroke With 30-Day NIHSS Score—Comparison With Diffusion and Perfusion MRI," Stroke. 2004;35-899-903.

Hossmann, K.-A. et al., "EEG Frequency Analysis in the course of Acute Ischemic Stroke," Neurosurg. Rev. 1980;3:31-36.

Hu, Xiao et al., "An algorithm for extracting intracranial pressure latency relatve to electrocardiogram R wave," Physiol. Meas. 2008;29:459-471.

Hwa, Rodolph C. et al., "Stroke detection based on the scaling properties of human EEG," Physica A. 2004;338:246-254.

Jachuck, S.J. et al., "Electrocardiographic Abnormalities Associated with Raised Intracranial Pressure," British Medical Journal. 1975;1:242-244.

Kanter, Merrill C. MD et al., "Carotid Stenosis in Patients With Atrial Fibrillation—Prevalence, Risk Factors, and Relationship to Stroke in the Stroke Prevention in Atrial Fibrillation Study," Arch Intern Med. 1994;154-1372-1377.

Krul, J.M. et al., "Stroke-related EEG Changes During Carotid Surgery," Eur J Vasc Surg. 1989;3:423-428.

Oppenheimer, Stephen MD, FRCP, "Neurogenic cardiac effects of cerebrovascular disease," Current Opinion in Neurology. 1994;7:20-24.

Van Putten, Michel J.A.M. MD, PhD et al., "Continuous Quantitative EEG Monitoring in Hemispheric Stroke Patients Using the Brain Symmetry Index," Stroke. 2004;35:2489-2492.

Grmec, S. et al., "Electrocardiographic changes in patients with acute stroke in the prehospital setting and their prognostic importance," Critical Care. 2006;10(Supp.1):457.

Hoshide, Satoshid MD et al., "Marked Elevation of the Segment in Cerebellar Hemorrhage," JAGS. 2005;53(10):1837-1349.

NIH, NIH Stroke Scale, National Institutes of Health, www.ninds.nih.gov/doctors/NIH_Stroke_Scale.pdf.

Ruel, Marc MD, MPH et al., "Late Incidence and Determinants of Stroke After Aortic and Mitral Valve Replacement," Ann Thorac Surg. 2004;78:77-83.

Sacco, Ralph L. MD et al., "Guidelines for Prevention of Stroke in Patients with Ischemic Stroke or Transient Ischemic Attach," Stroke. 2006;37:577-617.

Sakr, Yasser L. et al., "Relation of ECG changes to neurological outcome in patients with aneurysmal subarachnoid hemorrhage," International Journal of Cardiology. 2004;96:369-373.

Schuchert, A. et al., "Impact of Long-Term ECG Recording on the Detection of Paroxysmal Atrial Fibrillation in Patients After an Acute Ischemic Stroke," PACE. 1999;22:1082-1084.

Smith, McKamy MD et al., "Cardiac Arrhythmias, Increased Intracranial Pressure, and the Autonomic Nervous System," CHEST. 1972;61(2):125-133.

Tobis, Jonathan M. MD, et al. "Does Patent Foramen Ovale Promote Cryptogenic Stroke and Migraine Headache?" Tex Heart Inst J. 2005;32(3):362-365.

\* cited by examiner

SYSTEMS AND METHODS FOR USE BY AN IMPLANTABLE MEDICAL DEVICE FOR DETECTING AND DISCRIMINATING STROKE AND CARDIAC ISCHEMIA USING ELECTROCARDIAC SIGNALS AND HEMODYNAMIC PARAMETERS

CROSS REFERENCE TO RELATED APPLICATIONS

This application is related to U.S. patent application Ser. No. 12/366,526, filed Feb. 2, 2009, titled "Systems and Methods for Use with an Implantable Medical Device for Detecting Stroke Based on Electrocardiac Signals" and now U.S. Pat. No. 8,241,221.

FIELD OF THE INVENTION

The invention generally relates to implantable medical devices, such as pacemakers, implantable cardioverter/defibrillators (ICDs), cardiac resynchronization therapy device/defibrillators (CRT-Ds) and subcutaneous monitors, and, in particular, to techniques for detecting and distinguishing stroke and cardiac ischemia within patients in which such devices are implanted.

BACKGROUND OF THE INVENTION

A stroke is a sudden loss of brain function caused by a blockage of a blood vessel to the brain (ischemic stroke) or a rupture of a blood vessel to the brain (hemorrhagic stroke). Each year, more than 700,000 people in the U.S. alone suffer a new or recurrent stroke and the consequences can be devastating. Over 150,000 of these events end in death, and many of those who survive are left seriously and permanently impaired. During each minute of progression of a stroke, about two million brain cells die. Approximately fourteen billion brain cells die during the average ten-hour stroke. As such, the time from onset of a stroke to its diagnosis and treatment by medical personnel is critical.

Accordingly, it is highly desirable to provide techniques for detecting the onset of a cerebral stroke within a patient for promptly notifying family members, caregivers or emergency personnel. It is particularly desirable to detect stroke using an implantable medical device as many elderly patients prone to stroke already have such devices implanted therein or are candidates for such devices.

Useful techniques for detecting stroke using implantable medical devices are described in U.S. patent application Ser. No. 12/366,526, filed Feb. 5, 2009, to Park and entitled "Systems and Methods for use with an Implantable Medical Device for Detecting Stroke Based on Electrocardiac Signals," and now U.S. Pat. No. 8,241,221, the disclosure of which is hereby incorporated by reference. Briefly, techniques are provided therein for detecting stroke within a patient based on predetermined changes in an electrocardiac signal, such as changes within an electrocardiogram (ECG) sensed by a subcutaneous monitor or changes within an intracardiac electrogram (IEGM) signals sensed by a pacemaker or ICD. Exemplary features indicative of possible stroke include the onset of prominent U-waves, the onset of notched T-waves, and changes in ST segment duration or QT duration or dynamic trends in these parameters. In one example, a preliminary detection of stroke is performed by an implantable device based on an analysis of features of the ECG or IEGM. The device transmits a signal indicative of possible stroke to a bedside monitor or other external system, which generates a stroke questionnaire for use in confirming the stroke. Family members or other caregivers input answers to the questionnaire into the external system, which confirms or disconfirms the stroke. Emergency personnel can be automatically notified.

It would be desirable to provide additional or alternative techniques for detecting stroke using an implantable medical device, particularly techniques wherein the stroke can be confirmed based on additional signals detected within the patient, rather than based on a questionnaire answered by family members or other caregivers. It is to this end that aspects of the present invention are directed. It is also desirable to provide techniques for distinguishing stroke from cardiac ischemia from one another based on signals sensed using an implantable medical device. In this regard, certain changes in electrocardiac signals caused by stroke (such as changes in ST segment duration and in QT duration observed within ECGs or IEGMs) can also be caused by cardiac ischemia and hence there is a need to reliably distinguish stroke from cardiac ischemia when using electrocardiac signals. (Note that cardiac ischemia is distinct from an ischemic stroke. Cardiac ischemia is an ischemia occurring within the heart that affects heart function. Ischemic stroke is an ischemia occurring within the brain that affects brain function.)

SUMMARY OF THE INVENTION

In an exemplary embodiment, a method is provided for use with an implantable medical device for implant within a patient for distinguishing stroke from cardiac ischemia. The device senses electrocardiac signals within the patient, which are indicative of a possible stroke. In some examples, the electrocardiac signals are IEGM signals sensed via the leads of a pacemaker, ICD or CRT-D. In other examples, the electrocardiac signals are ECG signals sensed via a subcutaneous monitor such as a loop/recorder monitor. In either case, the device also detects hemodynamic parameters within the patient that are affected by possible cardiac ischemia. The hemodynamic parameters can include, e.g., cardiac contractility values or stroke volume values detected using suitable hemodynamic sensors implanted on or within the heart or thorax of the patient. The device then distinguishes stroke from cardiac ischemia within the patient based on the electrocardiac signals and the hemodynamic signals. Herein, cardiac ischemia includes myocardial infarction, which is a particularly severe form of cardiac ischemia.

In one example, IEGM signals sensed by a pacer/ICD are examined to detect a preliminary indication of stroke within the patient based on predetermined changes in the IEGM indicative of a possible stroke. Exemplary changes within an IEGM indicative of stroke include the onset of prominent U-waves, the onset of notched T-waves, changes in ST segment duration, and changes in QT duration and/or any dynamic changes (trends) in time in any of these signals. Upon detection of the preliminary indication of stroke, hemodynamic parameters affected by a possible cardiac ischemia are then detected. For example, a stroke volume sensor or a cardiac contractility sensor may be activated by the pacer/ICD. Based on the hemodynamic parameters detected by the sensors, the pacer/ICD then distinguishes stroke from cardiac ischemia. In one particular example, the pacer/ICD examines the hemodynamic parameters to identify changes consistent with cardiac ischemia. If the hemodynamic parameters exhibit changes consistent with cardiac ischemia, then stroke is thereby disconfirmed and an episode of cardiac ischemia is instead indicated. Conversely, if the hemodynamic parameters do not exhibit changes consistent with cardiac ischemia, then the preliminary indication of stroke is confirmed. In this manner, stroke is distinguished from cardiac ischemia.

In one particular example, to determine whether the hemodynamic parameters exhibit changes consistent with cardiac ischemia, the pacer/ICD detects a particular hemodynamic parameter that can be affected by cardiac ischemia, then compares the parameter against a corresponding baseline parameter previously detected within the patient during a time period without cardiac ischemia. The hemodynamic parameter is deemed to be consistent with cardiac ischemia if the detected parameter differs substantially from its baseline value. For example, if cardiac contractility is found to have decreased from a baseline contractility value, this change is deemed to be consistent with cardiac ischemia and so the preliminary indication of stroke is disconfirmed and ischemia is instead indicated. In another example, if stroke volume is found to have decreased from a baseline stroke volume, then the change is deemed to be consistent with cardiac ischemia and so ischemia is likewise indicated. If the hemodynamic parameters, however, have not changed significantly from their baseline values, then the preliminary indication of stroke is thereby confirmed.

Once stroke is distinguished from cardiac ischemia, appropriate therapy may be delivered by the pacer/ICD, depending up on the capabilities of the device. Warning signals may be generated. Diagnostic data may be stored for subsequent clinician review. If used in conjunction with a bedside monitor or other external monitoring device, suitable warning signals can provided to the family members or caregivers via the bedside monitor. The warning signals indicated whether stroke or cardiac ischemia has occurred. In some instances, particularly if stroke is severe, emergency personnel can be automatically notified via a suitable telephonic or computer network communication system. The patient's primary care physician can also be directly notified. In this manner, medical attention can promptly be provided to reduce the risk of death or permanent impairment due to the stroke.

Method and system examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of IEGM-Based Stroke/Ischemia Discrimination System

Figure 1:
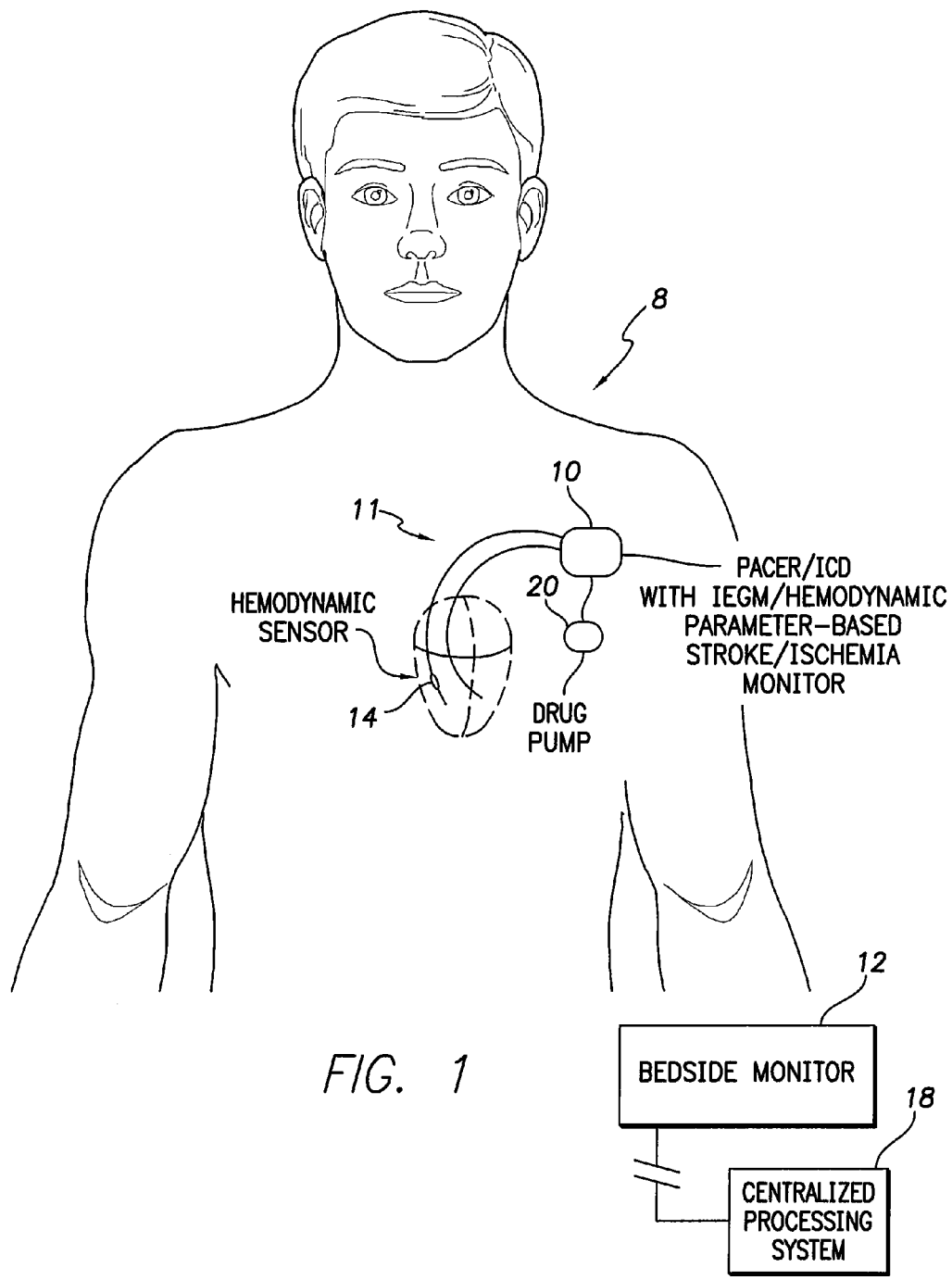
FIG. 1 illustrates pertinent components of a pacer/ICD equipped with an IEGM/hemodynamic parameter-based monitoring system capable of detecting and distinguishing stroke and cardiac ischemia.
Figure 5:
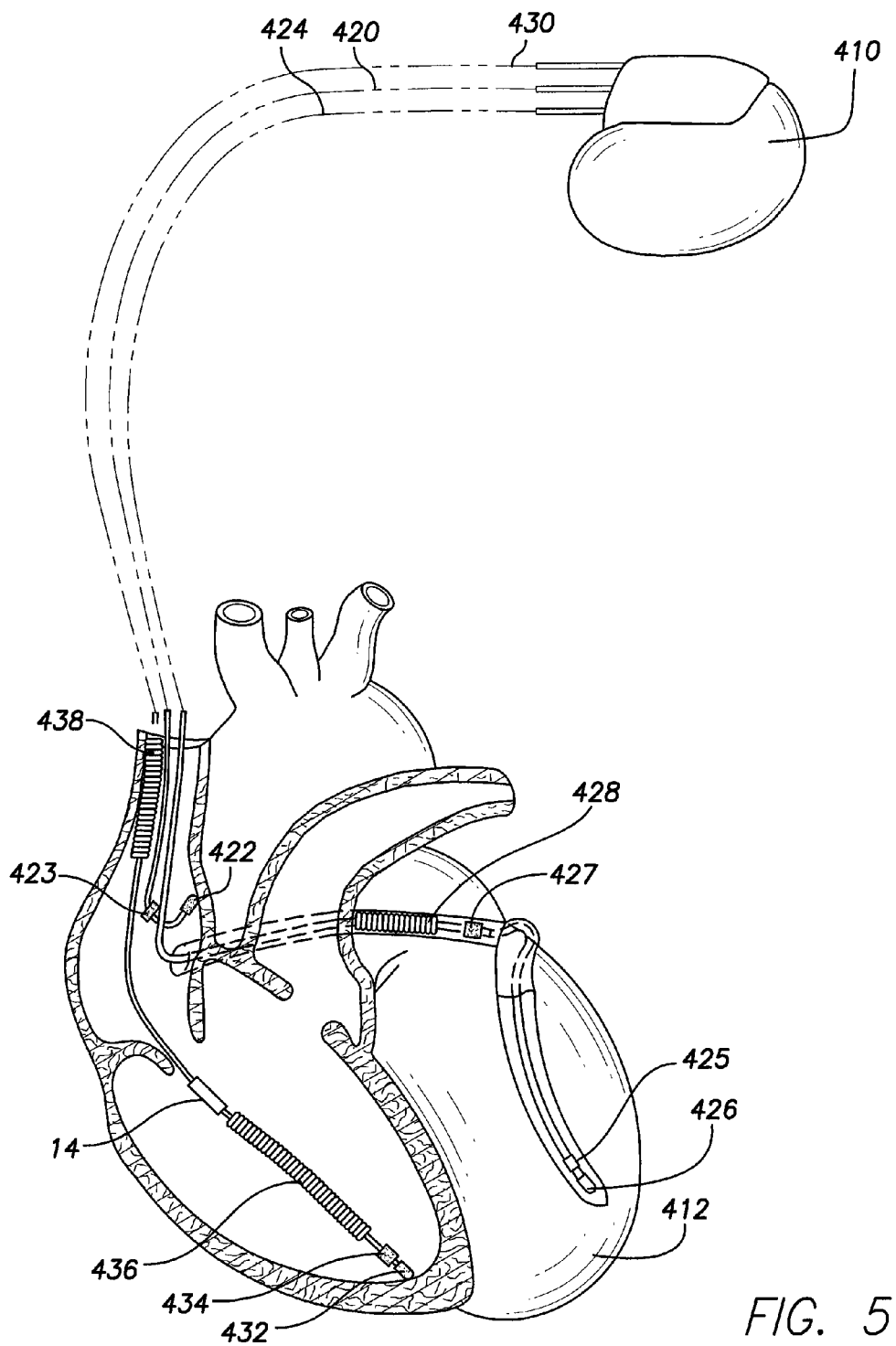
FIG. 5 is a simplified, partly cutaway view of the heart of a patient, illustrating the exemplary pacer/ICD of FIG. 1, along with a set of leads implanted in the heart of the patient.

FIG. 1 illustrates an implantable medical system 8 having a pacer/ICD 10 equipped with an IEGM/hemodynamic parameter-based stroke/ischemia monitor for distinguishing stroke from cardiac ischemia within the patient in which the system is implanted. Detection and discrimination of stroke and cardiac ischemia is achieved based on IEGM signals sensed via a set of leads 11 and selected hemodynamic parameters sensed via one or more hemodynamic sensors 14. Two leads—LV and RV—are shown in FIG. 1 (in stylized form) for sensing the IEGM signals. A more complete set of leads is illustrated in FIG. 5, described below. A single hemodynamic sensor 14 is also shown in FIG. 1. Additional hemodynamic sensors may be provided. Although the exemplary hemodynamic sensor of FIG. 1 is shown mounted to the RV lead, it should be understood that the actual location of the sensor will depend upon the particular hemodynamic parameter or parameters to be detected. As such, the location of the sensor of FIG. 1 is merely exemplary. Note also that, in some cases, the hemodynamic sensor will be a component of the pacer/ICD itself. This is particularly common for sensors configured to sense hemodynamic parameters based on an analysis of electrical signals detected using the leads 11. For example, certain hemodynamic sensors are designed to analyze impedance signals detected using the leads. This will be discussed in greater detail below.

Upon detection of stroke or cardiac ischemia, warning signals may be transmitted to a bedside monitor 12 or other external system alerting family members or caregivers of the condition. The bedside monitor can also forward warning signals or other suitable information via a centralized processing system 18 to the patient's primary care physician or, in some implementations, directly to emergency personnel. The centralized system may include such systems as the HouseCall™ remote monitoring system or the Merlin@home/Merlin.Net systems of St. Jude Medical.

Direct notification of emergency personnel might be particularly appropriate upon detection of a stroke so as to ensure prompt medical attention.

Warnings pertinent to stroke/cardiac ischemia may also be generated using a hand-held personal advisory module (PAM), not separately shown, or using an internal warning device provided within the pacer/ICD. The internal warning device can be a vibrating device or a "tickle" voltage device that, in either case, provides perceptible stimulation to the patient to alert the patient. If a PAM is employed, the PAM can provide audible or visual alarm signals to alert the patient or caregiver, as well as any appropriate textual or graphic displays. In addition, diagnostic information pertaining to the stroke/cardiac ischemia may be stored within the pacer/ICD for subsequent transmission to an external programmer (not shown in FIG. 1) for review by a clinician during a follow-up session between patient and clinician. The clinician then prescribes appropriate therapies including medications. The clinician may also adjust the operation of the pacer/ICD to activate, deactivate or otherwise control any therapies automatically provided by the device.

Also, in response to the detection of stroke or cardiac ischemia, therapy can be delivered to the patient by the implantable system. For example, the implantable system can be equipped with a subcutaneous drug pump 20 or other implantable drug dispensation device capable of the delivering medications directly to patient tissues. Implantable drug pumps for use in dispensing medications are discussed in U.S. Pat. No. 5,328,460 to Lord et al., entitled "Implantable Medication Infusion Pump Including Self-Contained Acoustic Fault Detection Apparatus." (This patent also discusses implantable "tickle" warning devices that may be used to deliver warning signals.)

Additionally, the pacer/ICD performs a wide variety of pacing and/or defibrillation functions, such as delivering routine pacing or generating and delivering shocks in response to ventricular fibrillation (VF.) Also, in some examples, the device is equipped to deliver CRT. Briefly, CRT seeks to normalize asynchronous cardiac electrical activation and resultant asynchronous contractions associated with congestive heart failure (CHF) by delivering synchronized pacing stimulus to both ventricles. The stimulus is synchronized so as to improve overall cardiac function. This may have the additional beneficial effect of reducing the susceptibility to life-threatening tachyarrhythmias.

Figure 2:
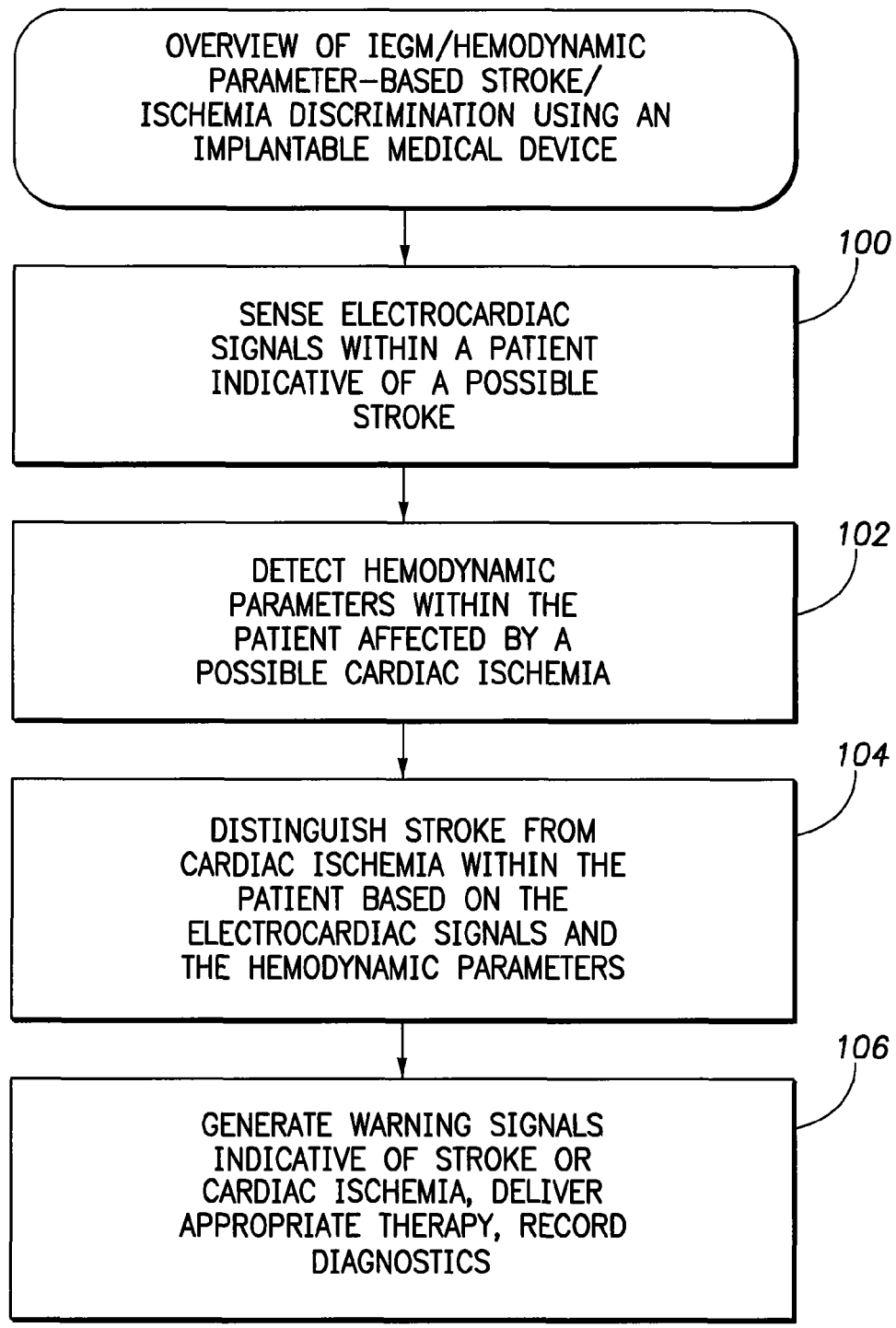
FIG. 2 provides an overview of the method for detecting and distinguishing stroke and cardiac ischemia performed by the system of FIG. 1, or by other suitably equipped implantable systems, which exploits changes/trends in electrocardiac signals and in selected hemodynamic parameters.

FIG. 2 broadly summarizes the stroke/cardiac ischemia detection and discrimination procedure implement by the pacer/ICD of FIG. 1 or other suitable equipped implantable medical systems. Initially, at step 100, electrocardiac signals are sensed or detected within a patient, which are indicative of a possible stroke within the patient. At step 102, the device detects hemodynamic parameters within the patient that are affected by a possible cardiac ischemia, such as stroke volume or cardiac contractility. At step 104, the device distinguishes stroke from cardiac ischemia within the patient based on the electrocardiac signals and the hemodynamic parameters. At step 106, the device generates warning signals indicative of stroke or cardiac ischemia, delivers appropriate therapy, records diagnostics or performs other suitable functions. Alternatively, these steps may be performed by other implantable medical systems, such as a suitably-equipped subcutaneous loop recorder/monitor (described below.)

Thus, FIGS. 1 and 2 provide a broad overview of the systems and methods of the invention. Embodiments may be implemented that do not necessarily perform all of the described functions. For example, embodiments may be implemented that provide, for example, for detecting and distinguishing stroke and cardiac ischemia and generating warnings but which do not automatically deliver therapy in response to the stroke or cardiac ischemia. Drug pumps are not necessarily implanted. Bedside monitors or PAMs are not necessarily used. Some implementations may employ some form of external device for generating warning signals but no internal warning device. Other embodiments might include additional implanted devices or components, such as neurostimulators for selectively stimulating portions of the brain or nervous system. These are just a few exemplary embodiments. No attempt is made herein to describe all possible combinations of components that may be provided in accordance with the general principles of the invention.

Also, note that, the particular shapes, sizes and locations of the implanted components shown in FIG. 1 are merely illustrative and may not necessarily correspond to actual implant locations. Preferred implant locations for the leads are more precisely illustrated in FIG. 5.

Exemplary Stroke/Cardiac Ischemia Detection and Discrimination Techniques

Figure 3:
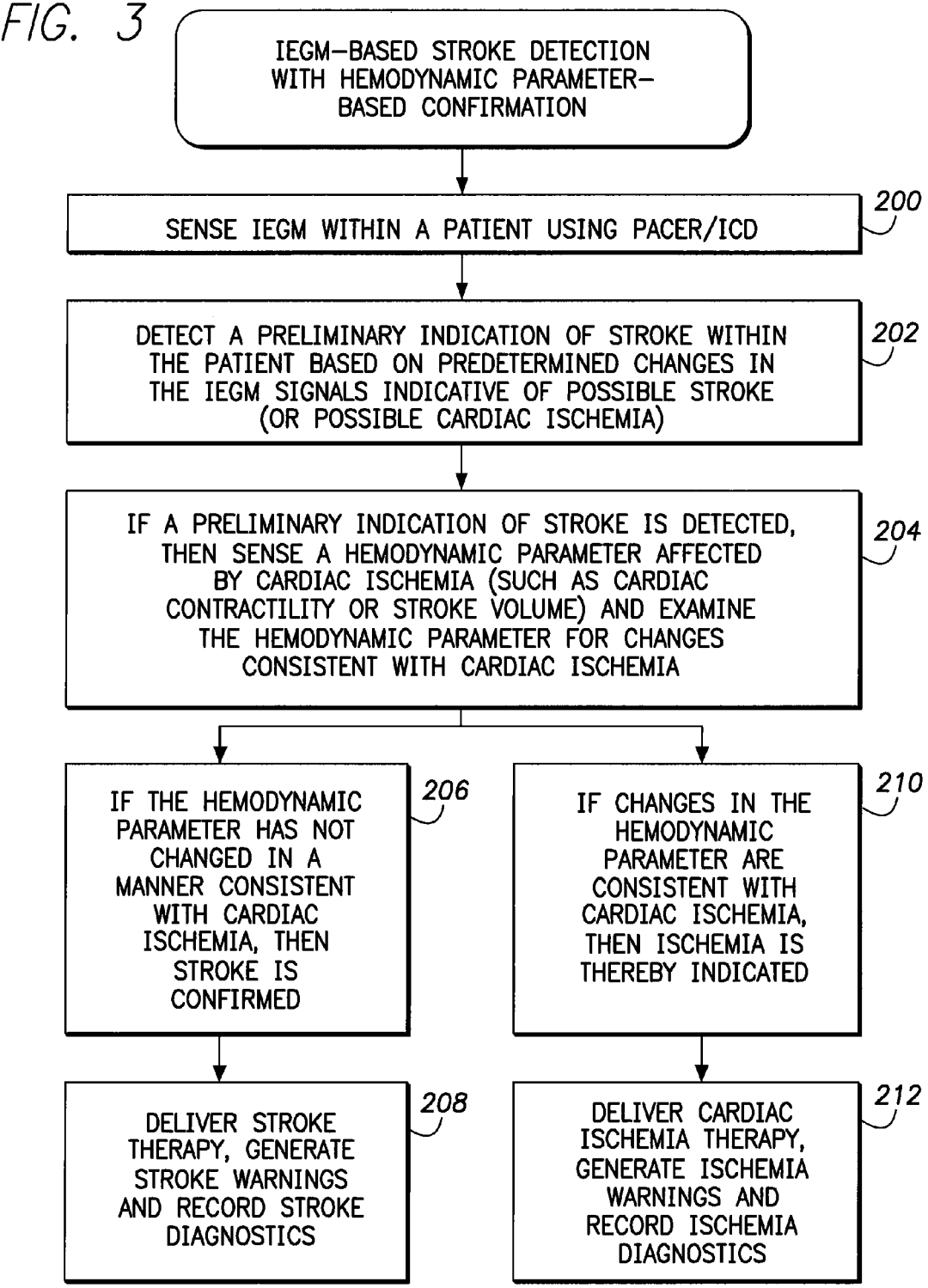
FIG. 3 illustrates an exemplary embodiment of the general technique of FIG. 2 for use with a pacer/ICD, wherein a preliminary detection of stroke made by the pacer/ICD triggers detection of hemodynamic parameters for discriminating stroke and cardiac ischemia.

FIG. 3 illustrates a stroke/ischemia detection and discrimination technique that exploits IEGM signals detected by a pacer/ICD to provide a preliminary indication of stroke. The pacer/ICD further utilizes hemodynamic parameters to confirm or disconfirm the stroke. Initially, at step 200, an IEGM is sensed within the patient continuously and in real-time using the leads of the pacer/ICD, such as by employing bipolar sensing in the RV and LV. At step 202, the device detects a preliminary indication of stroke within the patient based on predetermined changes or trends in the IEGM that are indicative of a possible stroke within the patient.

In this regard, whether ischemic or hemorrhagic, cerebral strokes can produce changes in the IEGM of a patient. These IEGM changes are likely due to extreme sympathetic neural stimulation associated with stroke, which in turn may be associated with raised intracranial pressures (ICPs) arising due to the stroke. In this regard, augmentation of intra-cardiac sympathetic nerve activity seems to occur, producing cardiac myocyte damage and depolarizing ionic shifts, resulting, e.g., in IEGM repolarization changes. Nevertheless, regardless of the physiological mechanism by which the stroke causes changes in the IEGM, these changes (or trends therein) are typically detectable within an IEGM so as to provide a preliminary indication of stroke.

Exemplary morphological changes in the IEGM indicative of stroke include the onset of prominent U-waves, the onset of notched T-waves, changes in ST segment duration, and changes in QT duration within an IEGM and/or any dynamic changes (trends) in time in any of these signals. (These are just some examples. In general, any of a variety of predetermined changes in the IEGM and/or predetermined dynamic changes/trends in time in parameters derived from the IEGM can be exploited.) U-waves are thought to represent electrical repolarization of the papillary muscles or Purkinje fibers. U-waves are not always present in the IEGM but can become prominent during a stroke. The T-wave of the IEGM corresponds to a cardiac ventricular repolarization event, i.e. it is an electrical signal produced during the repolarization of the ventricular myocardium following a ventricular contraction triggered by ventricular depolarization. The T-wave follows a ventricular depolarization event known as an R-wave or QRS-complex. T-waves are usually smooth in shape, but stroke can cause notches to appear within the T-waves. Herein, the ST segment refers to the interval from the end of the QRS-complex to the beginning of the subsequent T-wave. The QT interval refers to the interval from the start of the QRS-complex to the beginning of the T-wave. These and other morphological features of the IEGM can be detected, for example, using LV and RV IEGM signals sensed by pacer/ICD. Alternatively, similar features of an ECG can be detected via subcutaneous (subQ) implantable medical devices. See, FIGS. 7 and 8, described below.

As already explained, at least some IEGM changes indicative of stroke might also be indicative of a possible cardiac ischemia within the patient. In particular, changes in the ST segment duration and changes in QT duration can be caused by cardiac ischemia, as well as stroke. Accordingly, at step 204, if a preliminary indication of stroke has been detected by the pacer/ICD, then the pacer/ICD senses or detects at least one hemodynamic parameter affected by cardiac ischemia (such as cardiac contractility or stroke volume) and examines the hemodynamic parameter for changes consistent with cardiac ischemia. Mechanical synchrony might also be affected by cardiac ischemia.

If, at step 206, the hemodynamic parameter has not changed in a manner consistent with cardiac ischemia, then stroke is confirmed. For example, stroke volume and cardiac contractility both typically decrease due to cardiac ischemia. If there is no significant change in either, then the changes detected in the IEGM are deemed to have been caused by a stroke and not by a cardiac ischemia. In that case, at step 208, the pacer/ICD delivers stroke therapy, generates stroke warnings and/or records stroke diagnostics, depending upon device programming and on the particular capabilities of the device. In one particular example, the bedside monitor issues a loud alarm to notify family members or caregivers of the stroke. The warning signals can also be relayed to the patient's primary care physician or directly to emergency personnel such as, e.g., by directly calling 911 or other suitable emergency telephone numbers. For a severe stroke, direct notification of emergency personnel is preferred so as to achieve the quickest possible response. As already noted, about two million brain cells can die during each minute of progression of a stroke and so prompt medical attention is crucial. (The severity of the stroke may be evaluated, for example, based on the relative amount of change in the aforementioned IEGM parameters, with generally larger changes being indicative of a more severe stroke.)

Insofar as therapy is concerned, a variety of responses might be triggered in response to stroke, depending upon the capabilities of the implantable system. For example, suitable neurostimulation might be delivered via the spinal cord, baroreceptors or sympathetic nerves, again depending upon the capabilities of the device. Spinal cord stimulation via an implantable lead is discussed, e.g., in U.S. Pat. No. 7,099,718, to Thacker et al. Baro-receptor stimulation to control blood pressure is discussed in U.S. Pat. No. 6,050,952 to Hakki et al. Techniques for stimulating sympathetic nerves are discussed in U.S. Pat. No. 6,937,896, to Kroll, entitled, "Sympathetic Nerve Stimulator and/or Pacemaker."

As to possible medications, tPA tissue plasminogen activator or like compounds can be automatically delivered to help restore blood flow to the brain immediately following are stroke. (Note that tPA tissue plasminogen activator is a thrombolytic agent, i.e. a compound for breaking down clots). After the stroke event has ended, anticoagulants can be delivered to prevent subsequent stokes, particularly in patients known to have atrial fibrillation or a heart-valve disorder. Suitable versions of these or other compounds may be identified for dispensing via an implantable drug dispensing unit, drug infusion unit and/or drug pump under the control of the pacer/ICD. See, e.g., U.S. Pat. No. 7,235,530, to Blair et al., entitled "Kallikrein Inhibitors and Anti-Thrombolytic Agents and Uses Thereof," which discusses compounds suitable for delivery via a medication infusion pump.

These and other responses to stroke are discussed in, e.g., U.S. patent application Ser. No. 12/558,385, filed Sep. 11, 2009, by Bharmi et al., entitled "System and Method for use with an Implantable Medical Device for Detecting Stroke based on Physiological and Electrocardiac Indice", published as U.S. Patent Application Publication Number 2011-0066028-A1.

If the device is equipped with an alternative or secondary stroke detection system, it might be desirable in some implementations to confirm the detection of stroke using the alternative system before therapy is delivered. See, for example, the stroke detection techniques set forth in the application of Bharmi et al. A questionnaire, such as the type described in the above-cited application by Park (Ser. No. 12/366,526, now U.S. Pat. No. 8,241,221), might also be employed before therapy is delivered, if a caregiver or family member is available to answer the questions.

Conversely, if at step 210, the hemodynamic parameter has changed in a manner that is consistent with cardiac ischemia, then stroke is disconfirmed and cardiac ischemia is instead indicated. For example, if there is a significant reduction in either stroke volume or cardiac contractility, then the changes detected in the IEGM are deemed to have been caused by an episode of cardiac ischemia, not an episode of stroke. In that case, at step 212, the pacer/ICD delivers cardiac ischemia therapy, generates cardiac ischemia warnings and/or records cardiac ischemia diagnostics, depending, again, upon device programming and on the particular capabilities of the device.

Adjustments to pacing therapy in response to cardiac ischemia may involve, for example, reduction of a base pacing rate so as to prevent a relatively high programmed base rate from exacerbating the ischemia. Anti-thrombolytics or other medications can be delivered using an implanted drug pump, if one is provided. Routine experimentation may be employed to identify medications for treatment of cardiac ischemia that are safe and effective for use in connection with an implantable drug pump. In some implementations, prior to delivering therapy in response to cardiac ischemia, the pacer/ICD corroborates the detection of ischemia using other cardiac ischemia detection techniques. See, for example, the techniques described in U.S. Pat. No. 7,297,114, of Gill et al., entitled "System and Method for Distinguishing among Cardiac Ischemia, Hypoglycemia and Hyperglycemia using an Implantable Medical Device." See, also, U.S. patent application Ser. No. 12/016,166, filed Jan. 17, 2008, of Boileau et al., now U.S. Pat. No. 8,265,739, entitled "Systems and Methods for Distinguishing Cardiac Ischemia from Systemic Influences on IEGM Morphology using an Implantable Medical Device." See also, U.S. patent application Ser. No. 11/394,724, of Ke et al., filed Mar. 31, 2006, now U.S. Pat. No. 7,610,086, entitled "Ischemia Detection using T-wave Amplitude, QTmax and ST Segment Elevation and Pattern Classification Techniques."

Figure 4:
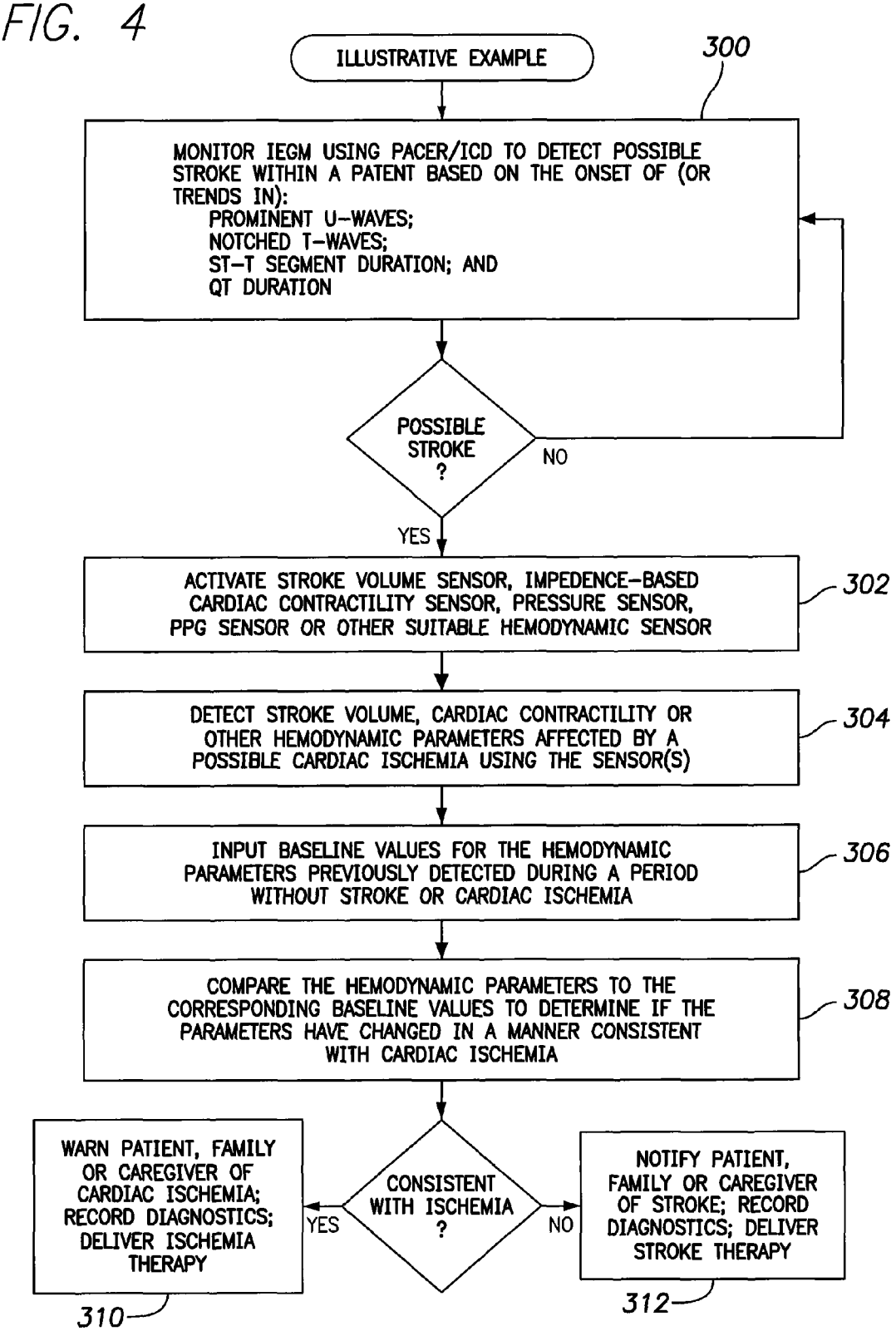
FIG. 4 provides a more detailed illustration of the technique of FIG. 3, particularly identifying IEGM parameters employed by the pacer/ICD to detect a preliminary indication of stroke, as well as identifying the particular hemodynamic parameters then used to discriminate stroke and cardiac ischemia.

FIG. 4 illustrates the technique of FIG. 3 in greater detail. At step 300, the pacer/ICD monitors the IEGM of the patient in which the device is implanted to detect possible stroke within a patient based on the onset of (or trends in): prominent U-waves; notched T-waves; ST segment duration; and QT duration. Otherwise conventional morphological event detection techniques may be used by the device to detect these features of the IEGM and quantify their size and/or duration. For U-waves, the device examines the portion of the IEGM where U-waves are expected to be found and, if U-waves are detected, the device then measures and quantifies the size and duration of the U-wave. For T-waves, the device examines the T-wave to detect any notches and, if present, measures and quantifies the depth and duration of the notches. For ST segment duration and QT duration, the device measures any changes in the duration of these intervals, either shortening or lengthening.

Once these or other IEGM features indicative of a possible stroke have been detected, the implantable device compares changes in the measured parameters against pre-determined thresholds indicative of stroke. Otherwise routine experimentation can be performed to identify, for each parameter, one or more suitable thresholds for use in detecting a preliminary indication of stroke. The thresholds may then be adjusted in view of baseline values obtained within the particular patient and updated periodically. Then, if all (or some) of the parameters cross their respective thresholds, a preliminary indication of stroke is thereby generated. In some implementations, only a single parameter needs to cross its threshold to trigger a preliminary indication of stroke. In other implementations, to avoid "false positives," two or more features are required to cross their respective features. Also, at step 300, trends in any of these parameters can be tracked and exploited. For example, the rate of change of ST segment duration or QT duration can be exploited, rather than merely their absolute values.

Assuming a possible stroke has been detected then, at step 302, the device activates one or more hemodynamic sensors within the patient such as a stroke volume sensor, an impedance-based cardiac contractility sensor, a pressure sensor, a photoplethysmography (PPG) sensor or other appropriate sensors such as heart sound sensors, etc. (In many cases, the sensors will already be active, since the device may be programmed to routinely detect and examine these hemodynamic parameters for reasons other than stroke detection.)

Stroke volume sensors are described in U.S. Pat. No. 6,961,615 to Kroll et al., entitled "System and Method for Evaluating Risk of Mortality due to Congestive Heart Failure using Physiologic Sensors." Impedance-based techniques for detecting stroke volume are discussed in U.S. Pat. No. 7,139,609 to Min et al., "System and Method for Monitoring Cardiac Function via Cardiac Sounds using an Implantable Cardiac Stimulation Device."

Techniques for detecting contractility are discussed in, e.g., U.S. Pat. No. 6,788,970 to Park et al., entitled "System and Method for Treating Vasovagal Syncope using Cardiac Pacing." As described therein, an implanted device can determined a patient's current contractility based on, for example, ventricular gradient, impedance, heart sounds, pre-ejection period (PEP), etc. For example, contractility may be measured using pressure waves. See, e.g., U.S. Pat. No. 6,208,900 to Ecker et al. and U.S. Pat. No. 4,485,813 to Anderson et al. Heart sound waves can also be used to determine contractility and other related parameters (e.g., stroke volume, blood pressure and dP/dt), as disclosed in U.S. Pat. No. 6,044,299 to Nilsson.

IEGM signals may also be a basis for determining contractility, e.g., using the IEGM to derive a "ventricular gradient" and QT interval. "Ventricular gradient," also sometimes referred to as "paced depolarization integral," is the integral of the paced R-wave (or P-wave) signal and is also believed to correlate to contraction force. See, for example, U.S. Pat. No. 4,759,366 to Callaghan.

Also, the pre-ejection period (PEP) can be examined. PEP, as taught in U.S. Pat. No. 4,719,921 to Chirife, is the sensing of the elapsed time from the ventricular depolarization corresponding to the QRS complex and the onset of ventricular ejection, which can be measured using the IEGM signal and a blood flow sensor, impedance sensor, or a ventricular volume detector, etc.

Impedance measurements of blood in the heart can also be employed to derive contractility of the myocardium and stroke volume. See, U.S. Pat. No. 4,884,576 to Alt and U.S. Pat. No. 4,535,774 to Olsen. Also, the rate of change in impedance (dZ/dt) has been shown to correspond to contractility. See, for example, U.S. Pat. No. 4,733,667 to Olive et al. and U.S. Pat. No. 5,800,467 to Park et al. Particularly effective "tri-phasic" impedance pulses for use in detecting impedance are discussed in U.S. patent application Ser. No. 11/558,194, of Panescu et al., filed Nov. 9, 2006, entitled "Closed-Loop Adaptive Adjustment of Pacing Therapy Based on Cardiogenic Impedance Signals Detected by an Implantable Medical Device." In some examples, surrogates for myocardial contractility are derived from cardiac pressure signals or PPG signals. See, for example, techniques described in U.S. patent application Ser. No. 12/405,090, filed Mar. 6, 2009 by Koh, entitled "System and Method for Controlling Rate-Adaptive Pacing based on a Cardiac Force-Frequency Relation detected by an Implantable Medical Device."

At step 304, the pacer/ICD then detects stroke volume, cardiac contractility or other hemodynamic parameters affected by a possible cardiac ischemia using signals received from the various sensors. At step 306, the pacer/ICD inputs baseline values for the various hemodynamic parameters that had been previously detected within the patient during sinus rhythm during a period without stroke or cardiac ischemia and stored in memory. In some examples, different baseline values can be detected and stored under different patient conditions, such as based on sinus rate, paced rate, activity state, circadian state, etc. At step 308, the pacer/ICD then compares the hemodynamic parameters to the corresponding baseline values to determine if the parameters have changed in a manner consistent with cardiac ischemia. For example, if stroke volume has decreased by at least a predetermined percentage from its baseline value, such as at least 50%, this is deemed to be consistent with cardiac ischemia. As another example, if contractility has decreased by at least a predetermined percentage from its baseline value, such as at least 50%, this is likewise deemed to be consistent with cardiac ischemia. These values are merely exemplary. Preferred or optimal threshold values can be obtained by evaluating changes in stroke volume/contractility during known episodes of cardiac ischemia in patients.

If a change is detected in the hemodynamic parameters that is consistent with cardiac ischemia, then at step 310, the pacer/ICD generates warning signals to warn the patient, family or caregiver of the cardiac ischemia; records diagnostics; and/or delivers cardiac ischemia therapy, as already discussed. Conversely, if the hemodynamic parameters have not changed in a manner consistent with cardiac ischemia, then at step 312, the pacer/ICD generates warning signals to warn the patient, family or caregiver of stroke; records diagnostics; and/or delivers stroke therapy, as already discussed. Depending upon the implementation, warning signals can be transmitted directly from the implanted device to the bedside monitor or other external device. In other implementations, a telemetry wand or other portable relay device may be exploited to aid in routing signals from the implanted device to the bedside monitor. Given that the patient might be incapacitated by the stroke, relatively long-range telemetry capability is preferred to ensure the signals are received by the bedside monitor or other external stroke confirmation system.

The above-described techniques can be implemented with a variety of implantable medical devices. For the sake of completeness, a pacer/ICD implementation will now be described in detail.

Exemplary Pacemaker/ICD

Figure 6:
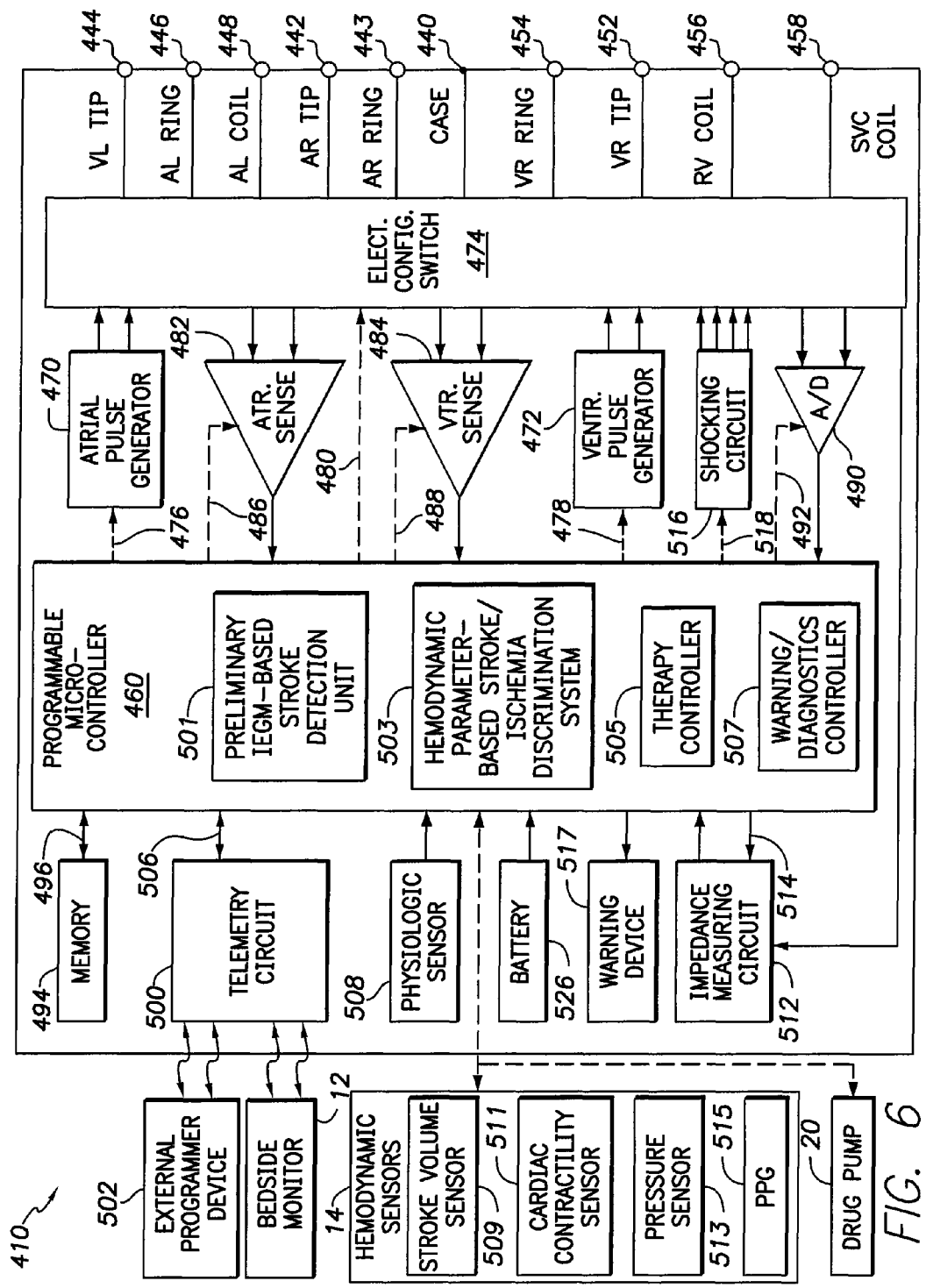
FIG. 6 is a functional block diagram of the pacer/ICD of FIG. 5, illustrating basic device circuit elements that provide cardioversion, defibrillation and/or pacing stimulation in four chambers of the heart, and particularly illustrating components within the device for detecting and discriminating stroke from cardiac ischemia based on IEGM signals and hemodynamic parameters.

With reference to FIGS. 5 and 6, a description of an exemplary pacer/ICD will now be provided, which is equipped to detect and distinguish stroke and cardiac ischemia within the patient based on an analysis of the IEGM of the patient in conjunction with hemodynamic signals. FIG. 5 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a right atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, and left ventricular ring electrode 425, left atrial pacing therapy using at least a left atrial ring electrode 427, and shocking therapy using at least a left atrial coil electrode 428. With this configuration, biventricular pacing can be performed. Although only three leads are shown in FIG. 5, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A general physiological sensor 14 is shown mounted to the RV lead. This sensor is merely exemplary. The actual location of the sensor will depend upon the particular hemodynamic parameters to be detected and, as such, the sensor might instead be mounted to the LV/CS lead near the LV or the LA, or near one of the major arteries or veins, such as the aorta. As already explained, in some cases, the hemodynamic sensor will be a component of the pacer/ICD itself. This is particularly common for sensors configured to sense hemodynamic parameters based on an analysis of impedance signals.

A simplified block diagram of internal components of pacer/ICD 410 is shown in FIG. 6. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned stroke/cardiac ischemia detection and discrimination.

The housing or case of 440 for pacer/ICD 410, shown schematically in FIG. 6, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

The hemodynamic sensor 14 is shown as including or incorporating a stroke volume sensor 509, a contractility sensor 511, a pressure sensor 513 and a PPG sensor 515. As can be appreciated, more or fewer sensors can be provided. The sensors can be physically separate from one another. Also, additional terminals may be provided for use with the various hemodynamic sensors (which, for simplicity, are shown functionally connected to the pacer/ICD via a dashed line.)

An integrated sensor providing a variety of sensor functions is described in U.S. patent application Ser. No. 11/927,026, filed Oct. 29, 2007, by Nabutovsky et al. Sensors exploiting micro-electro-mechanical system (MEMS) technology is described in U.S. patent application Ser. No. 11/856,443, by Zhao, filed Sep. 17, 2007, entitled "MEMS-Based Left Atrial Pressure Sensor for use with an Implantable Medical Device."

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 6, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial and ventricular sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain/sensitivity control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 524 in telemetric communication with the external device 502, such as a programmer, transtelephonic transceiver or a diagnostic system analyzer. The telemetry circuit 524 is activated by the microcontroller by a control signal 506. The telemetry circuit 524 advantageously allows intracardiac electrograms and status information relating to the operation of pacer/ICD 410 (as contained in the microcontroller 460 or memory 494) to be sent to the external device 502 through an established communication link 504. The telemetry circuit also transmits signals to bedside monitor 12, including the aforementioned stroke indication signal.

Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV delay, V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 526, which provides operating power to all of the circuits shown in FIG. 6. The battery 526 may vary depending on the capabilities of pacer/ICD 410. For pacer/ICD 410, which employs shocking therapy, the battery 526 should be capable of operating at low current drains for long periods, and then be capable of providing high-current pulses (for capacitor charging) when the patient requires a shock pulse. The battery 526 must also have a predictable discharge characteristic so that elective replacement time can be detected. Accordingly, pacer/ICD 410 is preferably capable of high voltage therapy and appropriate batteries.

As further shown in FIG. 6, pacer/ICD 410 is shown as having an impedance measuring circuit 512 which is enabled by the microcontroller 460 via a control signal 514. Uses for an impedance measuring circuit include, but are not limited to, detecting contractility as discussed above, as well as, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; and detecting the opening of heart valves, etc. The impedance measuring circuit 512 is advantageously coupled to the switch 474 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 or more joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 or more joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Insofar as stroke detection is concerned, the microcontroller includes a preliminary IEGM-based stroke detection unit 501 operative to detect a preliminary indication of stroke based on an analysis of the IEGM of the patient, including T-waves, U-waves (if present), ST segments, and QT segments. The microcontroller also includes a hemodynamic parameter-based stroke/ischemia discrimination system 503, which is operative to distinguish stroke from cardiac ischemia within the patient based on the IEGM signals and one or more hemodynamic parameters detected by the device, such as by sensor 14. A therapy controller 505 controls therapy, when appreciate, based on the detection of stroke, cardiac ischemia or other medical conditions. As one example, the pacing rate being applied to the heart may be reduced in response to a stroke so as to reduce the risk of exacerbating the stroke or by delivering appropriate medications via drug pump 20. A warning/diagnostics controller 507 controls the generation of warning signals (via, e.g., a warning device 517) and the recording of diagnostics (using memory 494.)

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

In an alternative implementation, the implantable medical device includes or comprises a Confirm™ monitor provided by St. Jude Medical, modified for use with at least one hemodynamic sensor capable of sensing a hemodynamic parameter affected by cardiac ischemia. This device is adapted for subcutaneous implant, particularly within patients suspected of suffering episodes of atrial fibrillation (AF.) The device is thus preferably equipped to detect both AF (and other possible arrhythmias) as well as possible stroke. AF increases the risk of ischemic stroke due to thrombosis and so the incorporation of stroke monitoring with a subcutaneous AF monitor is highly desirable. When implemented via a subcutaneous device, the device senses ECG signals rather than IEGM signals and detects the preliminary indication of stroke based n the ECG signals. Note that the ECG sensed by a subcutaneous device can differ somewhat from that of an IEGM sensed via cardiac pacing/sensing leads. Nevertheless, morphological features corresponding to those of an IEGM can be identified within the subcutaneously-sensed ECG.

Exemplary Subcutaneous Implantable Monitor with AF and Stroke Detection

Figure 7:
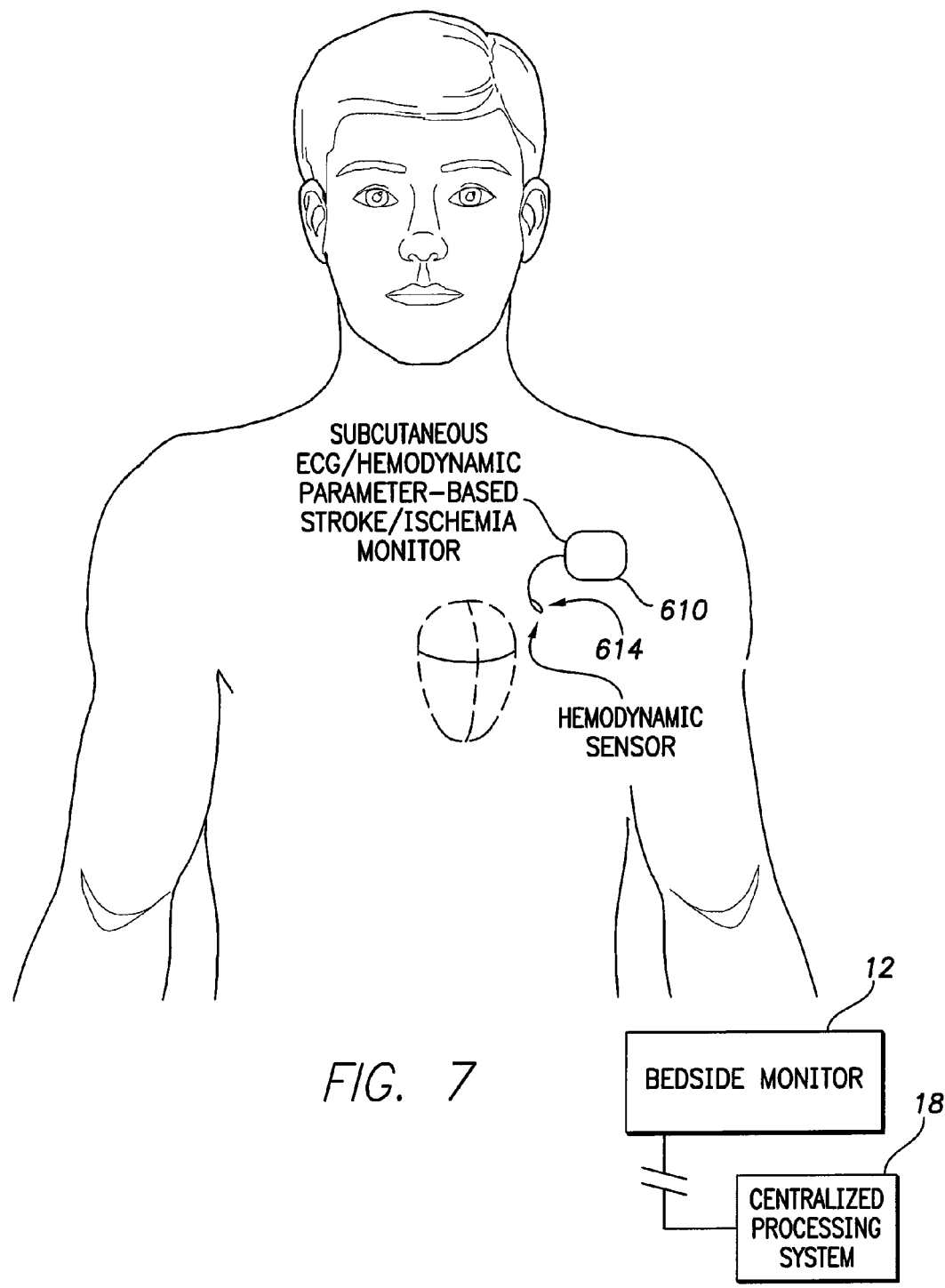
FIG. 7 illustrates pertinent components of a subcutaneous implantable monitor equipped with an ECG/hemodynamic parameter-based monitor system capable of detecting and distinguishing stroke and cardiac ischemia.
Figure 8:
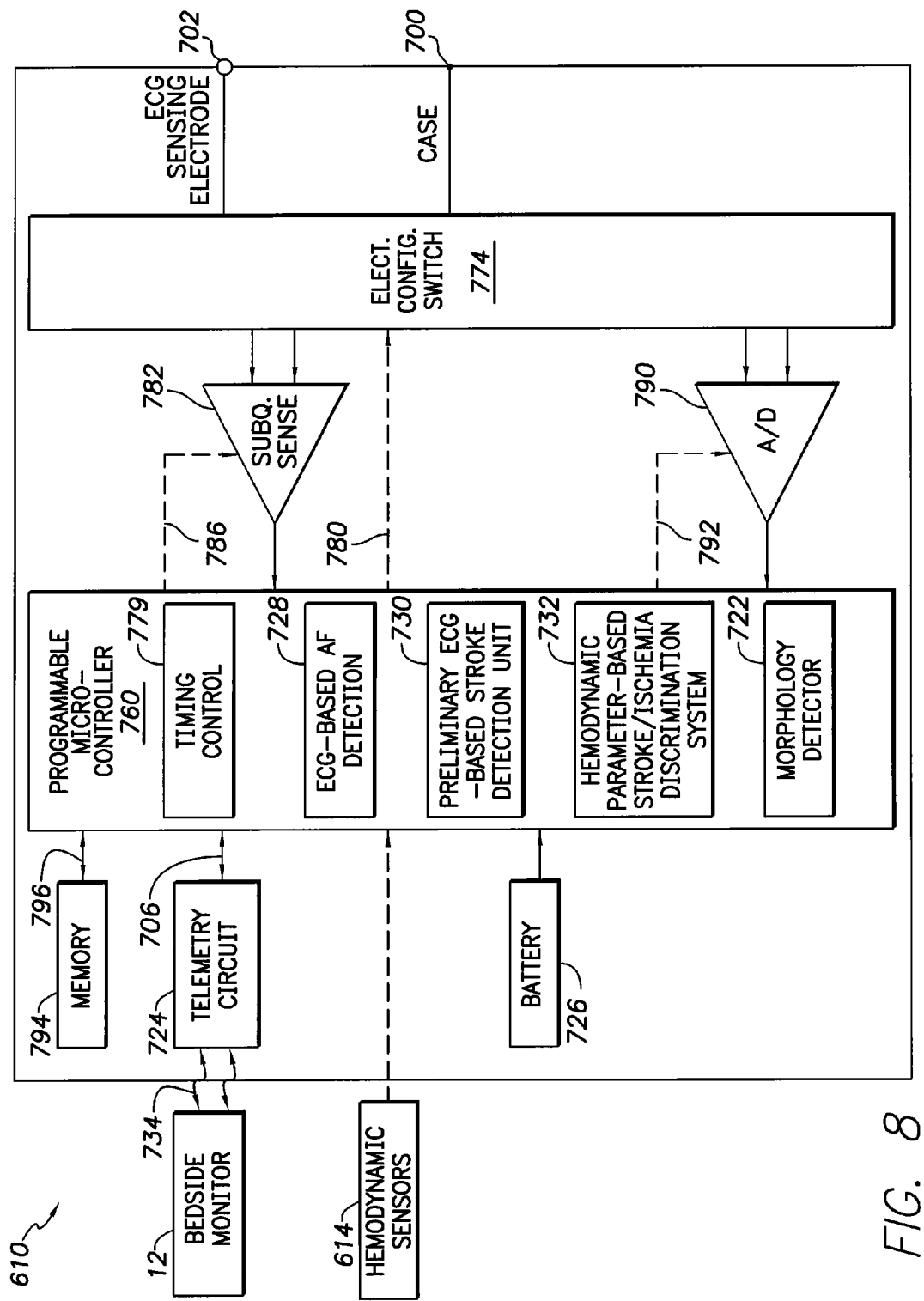
FIG. 8 is a functional block diagram of the subcutaneous implantable monitor of FIG. 7 for detecting and distinguishing stroke and cardiac ischemia based on ECG signals and hemodynamic parameters.

For the sake of completeness, internal components of an exemplary implantable monitor for use as stroke monitor 610 of FIG. 1 will now be summarized with reference to FIGS. 7 and 8. This device is equipped to monitor for AF as well as stroke/cardiac ischemia. Briefly, FIG. 7 illustrates an implantable medical system having a subcutaneously-implanted ECG/hemodynamic parameter-based stroke/ischemia monitor 610 for detecting and distinguishing stroke and ischemia within the patient based on an analysis of ECG signal and hemodynamic signals sensor by a hemodynamic sensor 614. Depending upon the particular hemodynamic sensor to be detected, the sensor might also be implanted subcutaneously or closer in proximity to the heart. A bedside monitor 12 or other external system may be used to receive warning signals/diagnostics from the implanted device.

Turning now to FIG. 8, pertinent components of the subcutaneous monitor are shown. A housing 700 (shown schematically) of the monitor 610 includes a connector having one or more ECG sensor terminals 702 adapted for connection to subcutaneous (SubQ) ECG sensors mounted to (or connected to) the exterior housing of the device. The housing (often referred to as the "can", "case" or "case electrode") can also act as the return (common) electrode, or anode, for any sensing electrodes implanted separately from the device. Only one ECG sensing electrode terminal is shown, but additional terminals can be provided to accommodate additional sensing electrodes or sensing leads.

At the core of the monitor 610 is a programmable microcontroller 760, which controls AF detection and stroke detection. The microcontroller 760 includes a microprocessor, or equivalent control circuitry, designed specifically for detecting AF and/or stroke and may further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design and operation of the microcontroller 760 are not critical to the invention. Rather, any suitable microcontroller 760 may be used that carries out the functions described herein. The use of microprocessor-based control circuits for performing timing and data analysis functions is well known in the art.

A switch bank 774 includes a plurality of switches for switchably connecting the ECG electrodes (assuming there is more than one) to the appropriate I/O circuits, thereby providing complete electrode programmability. A sense amplifier 782 is coupled to the ECG electrodes through switch bank 774 for detecting electrical cardiac activity. Sense amplifier 782 is capable of sensing signals in accordance with otherwise conventional techniques. The switch bank 774 determines the "sensing polarity" of the cardiac signal by selectively closing the appropriate switches, as is also known in the art. In this way, the clinician may program the sensing polarity. Sense amplifier 782 preferably employs a low power, precision amplifier with programmable gain and/or automatic gain control and/or automatic sensitivity control, bandpass filtering, and a threshold detection circuit, known in the art, to selectively sense electrical signals of interest. The automatic gain control, if implemented, enables the monitor 610 to deal effectively with the difficult problem of sensing any low frequency, low amplitude signal characteristics. The gain control is actuated by the programmable microcontroller 760. The gains are controlled on sense amplifier 782 by the microcontroller using control line 786. The outputs of the sense amplifier are connected to microcontroller 760.

For AF detection, the invention utilizes the sense amplifier to sense electrical signals to determine whether a cardiac rhythm is physiologic or pathologic. As used herein, "sensing" is reserved for the noting of an electrical depolarization, and "detection" is the processing of sequential sensed depolarization signals potentially in conjunction with the sensor input to establish a diagnosis of an arrhythmia. The timing intervals between sensed events (e.g., P-P intervals) are detected by a timing control unit 779 of microcontroller 760 and then classified by an ECG-based AF detection unit 728 by, for example, comparing the intervals to predefined rate zone limits indicative of AF.

The microcontroller also includes a preliminary ECG-based stroke detection unit 730, which performs the above-described preliminary stroke detection based on ECG morphological parameters (T-waves, U-waves, etc), as detected by a morphology detector 722. A hemodynamic parameter-based stroke/ischemia discrimination system 732 is operative to distinguish stroke from cardiac ischemia within the patient based on the IEGM signals and one or more hemodynamic parameters detected by the device, such as by sensor 614.

ECG signals and other sensed signals are also applied to the inputs of an analog to digital (A/D) data acquisition system 790. The gain of the ND converter 790 is controlled by the microprocessor 760 by signals along control line 792 in order to match the signal amplitude and/or the resolution to a range appropriate for the function of the A/D converter 790. The data acquisition system 790 is configured to acquire ECG signals, convert the raw analog data into a digital signal, and store the digital signals for later processing and/or telemetric transmission to bedside monitor 12. The data acquisition system 790 is coupled to the ECG electrode 702 through switch bank 774 to sample cardiac signals. The microcontroller 760 is further coupled to a memory 794 by a suitable data/address bus 796, wherein the programmable operating parameters used by the microcontroller 760 are stored and modified, as required, in order to customize the operation of device 610 to suit the needs of a particular patient. Such operating parameters define, for example, the particular parameters to be used to detect stroke or AF.

The operating parameters of the subcutaneous device 610 may be non-invasively programmed into the memory 794 through telemetry circuit 724 in telemetric communication with bedside monitor 12 or other external device, such as a programmer, transtelephonic transceiver, or a diagnostic system analyzer. The telemetry circuit 724 is activated by the microcontroller 760 by a control signal 706. The telemetry circuit 724 advantageously allows SubQ ECG electrograms and status information relating to the operation of device 610 (as contained in the microcontroller 760 or memory 794) to be sent to bedside monitor 12 through an established communication link 734, and then on to a centralized processing system 14, where appropriate.

The implantable monitor additionally includes a battery 726 that provides operating power to all of the circuits shown in FIG. 8. The battery is capable of operating at low current drains for long periods of time for monitoring. The battery 726 also should have a predictable discharge characteristic so that elective replacement time can be detected.

The principles of the invention may be exploiting using other implantable systems or in accordance with other techniques. Thus, while the invention has been described with reference to particular exemplary embodiments, modifications can be made thereto without departing from scope of the invention. Note also that the term "including" as used herein is intended to be inclusive, i.e. "including but not limited to."

What is claimed is:

1. A method for use with an implantable medical device for implant within a patient, said method comprising:
    sensing electrocardiac signals within the patient indicative of a possible stroke;
    detecting hemodynamic parameters within the patient affected by a possible cardiac ischemia; and
    distinguishing stroke from cardiac ischemia within the patient based on the electrocardiac signals and the hemodynamic parameters.

2. The method of claim 1 further comprising detecting a preliminary indication of stroke within the patient based on predetermined changes in the electrocardiac signals indicative of possible stroke.

3. The method of claim 2 wherein detecting the preliminary indication of stroke comprises detecting one more of the onset of prominent U-waves, the onset of notched T-waves, changes in ST segment duration, and changes in QT duration.

4. The method of claim 3 wherein detecting the preliminary indication of stroke comprises detecting trends toward one more or more of increasingly prominent U-waves, increasingly notched T-waves, changing ST segment durations, and changing QT durations.

5. The method of claim 2 wherein detecting hemodynamic parameters within the patient is performed upon detection of the preliminary indication of stroke.

6. The method of claim 5 wherein distinguishing stroke from cardiac ischemia comprises:
    examining the hemodynamic parameters for changes consistent with cardiac ischemia;
    generating a signal indicative of stroke if the hemodynamic parameters are not consistent with cardiac ischemia; and
    generating a signal indicative of cardiac ischemia if the hemodynamic parameters are indicative of cardiac ischemia.

7. The method of claim 6 wherein examining the hemodynamic parameters for changes consistent with cardiac ischemia comprises:
- comparing a selected hemodynamic parameter against a corresponding baseline parameter previously detected within the patient during a time period without cardiac ischemia; and
- determining that the selected hemodynamic parameter is consistent with cardiac ischemia if the parameter differs substantially from its baseline value.

8. The method of claim 7 wherein the selected hemodynamic parameter comprises one or more of a cardiac contractility parameter and a stroke volume parameter.

9. The method of claim 1 wherein sensing the electrocardiac signals comprises sensing signals representative of an intracardiac electrogram (IEGM).

10. The method of claim 9 wherein the implantable device comprises an implantable cardiac rhythm management device and wherein sensing the electrocardiac signals sensed is performed to sense signals representative of the IEGM using the implantable cardiac rhythm management device.

11. The method of claim 1 wherein sensing the electrocardiac signals comprises sensing signals representative of an electrocardiogram (ECG).

12. The method of claim 11 wherein the implantable device is a subcutaneously-implantable monitoring device and wherein sensing the electrocardiac signals is performed to sense signals representative of the ECG using the subcutaneously-implantable monitoring device.

13. A method for use with an implantable medical device for implant within a patient, said method comprising:
- sensing electrocardiac signals using the implantable device;
- detecting a preliminary indication of stroke within the patient based on predetermined changes in the electrocardiac signals indicative of possible stroke;
- if a preliminary indication of stroke is detected, then sensing a hemodynamic parameter within the patient affected by cardiac ischemia and examining the hemodynamic parameter for changes consistent with cardiac ischemia;
- confirming the stroke if changes in the hemodynamic parameter are not consistent with cardiac ischemia; and
- disconfirming the stroke if changes in the hemodynamic parameter are consistent with cardiac ischemia.

* * * * *